United States Patent [19]
Colodney et al.

[11] 3,944,661
[45] Mar. 16, 1976

[54] DENTIFRICES CONTAINING IRIDESCENT FLAKES

[75] Inventors: Daniel Colodney, Somerville, N.J.; John J. Steinke, Fayetteville, N.Y.; Robert Mitchell, Somerset, N.J.

[73] Assignee: Colgate-Palmolive Company, New York, N.Y.

[22] Filed: Aug. 5, 1974

[21] Appl. No.: 494,480

Related U.S. Application Data

[63] Continuation of Ser. No. 319,947, Dec. 29, 1972, abandoned, which is a continuation-in-part of Ser. No. 287,185, Sept. 5, 1972, abandoned, which is a continuation of Ser. No. 120,697, March 3, 1971, abandoned, which is a continuation-in-part of Ser. No. 54,575, July 13, 1970, abandoned.

[52] U.S. Cl. ................................................ 424/49
[51] Int. Cl.² ........................................... A61K 7/16
[58] Field of Search ............................... 424/49–58

[56] References Cited
UNITED STATES PATENTS

| 50,578 | 10/1865 | Hamilton et al. | 424/49 |
|---|---|---|---|
| 801,317 | 10/1905 | James | 424/49 |
| 2,059,396 | 11/1936 | Ripert | 424/49 |

FOREIGN PATENTS OR APPLICATIONS

| 449,713 | 6/1949 | Italy | 424/49 |
|---|---|---|---|

OTHER PUBLICATIONS

Durham, *American Perfumer and Cosmetics*, Vol. 82, pp. 31 & 32, July, 1967.

*Primary Examiner*—Richard L. Huff
*Attorney, Agent, or Firm*—Robert L. Stone; Murray M. Grill; Herbert S. Sylvester

[57] ABSTRACT

A dentifrice containing small proportions of mother of pearl flakes or other iridescent flakes.

6 Claims, No Drawings

DENTIFRICES CONTAINING IRIDESCENT FLAKES

This application is a continuation of Ser. No. 319,947, filed Dec. 29, 1972, which is a continuation-in-part of Ser. No. 287,185, filed Sept. 5, 1972, which is a continuation of Ser. No. 120,697, filed Mar. 3, 1971, which is a continuation-in-part of Ser. No. 54,575, filed July 13, 1970, all now abandoned.

One aspect of this invention relates to a dentifrice comprising a transparent toothpaste in which iridescent flakes, in small amount, are dispersed. The invention provides a toothpaste of unique sparkling appearance having very good characteristics as a dentifrice, such as superior stain removal properties.

Transparent toothpastes, which are well known in the art, generally contain a dental vehicle which forms a gel or creamy mass of a consistency which can be desirably extruded from a collapsible tube such as an aluminum tube, or a lead tube.

The vehicle, often referred to as a gelled vehicle, usually contains liquids and solids. In general, the liquid comprises water and/or a humectant such as glycerine, sorbitol, propylene glycol or polyethylene glycol 400 including suitable mixtures thereof. It is usually advantageous to use a mixture of both water and one or two humectants. The total liquid content is generally about 20–90% by weight of the vehicle. The preferred humectants are glycerine and sorbitol. Typically, the vehicle contains 0–80% by weight of glycerine, about 20–80% by weight of sorbitol and about 20–80% by weight of water.

The solid portion of the vehicle is a gelling agent, such as the natural and synthetic gums and gum-like materials, such as Irish Moss, gum tragacanth, alkali metal (e.g. Li, K or Na) carboxymethyl cellulose and hydroxymethyl carboxyethyl cellulose, polyvinyl pyrrolidone, starch, water soluble hydrophilic colloidal carboxyvinyl polymers such as those sold under the trademark Carbopol 934 and 940, hydroxyethyl cellulose, Indian gum, acacia gums, agar agar, locust bean gum, Laponite CP or SP, which are each synthetic inorganic complex silicate clays sold under trademark, by Laporte Industries, Ltd., and pectin or inorganic thickeners such as colloidal silica such as synthetic finely divided silicas including those sold under the trademarks Cab-O-Sil M5, Syloid 244, Syloid 266 and Aerosil D200. The solid portion of the vehicle is typically present in an amount up to about 10% by weight of the toothpaste and preferably about 0.5–5% by weight.

The art is well acquainted with the formulation of transparent dental gelled vehicles and the adjustments in composition needed to promote transparency. For instance, it is known that the presence of flavoring materials insoluble in the system will decrease transparency and that appropriate changes, e.g. in the surfactant system to increase the solubility of such flavoring materials will increase transparency.

The transparent toothpaste preferably also contains a dental polishing agent. The type and proportion of this polishing agent should be such as not to destroy the transparency of the toothpaste. One particularly suitable material is a porous amorphous silicic anhydride having an average particle size of about 1–65 microns, a surface area of about 200–450 $m^2/g$ and a bulk density of about 0.15–0.30 $g/cm^3$. Such an amorphous silicic anhydride contains but little water, typically about 5% or less, and is often referred to as a dehydrated silica gel. The preferred grades of amorphous silicic anhydride polishing agent are Syloid 72 and Syloid 74 which are described in "The Davison Family of Syloid Silicas" published by their manufacturer, Grace, Davison Chemical Co. Santocel 100, manufactured by Monsanto, is also a desirable polishing agent. Syloid 72 has an average particle size of about 4 microns, a surface area of about 340 $m^2/g$ and a bulk density of about 0.177 $g/cm^3$. Syloid 74 has an average particle size of about 8 microns, and a surface area of about 321 $m^2/g$ and a bulk density of about 0.6 $g/cm^3$. A grade of Santocel 100 has an average particle size of about 46–64 microns, a surface area of about 239 $m^2/g$ and a bulk density of about 0.24 $g/cm^3$. Other amorphous silicic anhydrides having surface areas greater than 450 $g/cm^3$ and even greater than 600 $g/cm^3$, such as Syloid 63 which is also described in "The Davison Family of Syloid Silicas" published by Grace, Davison Chemical Co., may also be used. These amorphous silicic anhydrides may be used singly or in mixtures. They are typically employed in amount of about 5–50%, preferably about 10–20% of the transparent toothpaste. The maximum particle size in the preferred grades of amorphous silicic anhydride polishing agent is desirably below the minimum size of palpability and is typically less than 75 microns. It is within the broad scope of the invention to use other polishing agents particularly those which have a refractive index similar to that of the vehicle.

An additional highly desirable polishing agent which may be added to the gel vehicle is a complex sodium alumino-silicate which has a refractive index of about 1.44–1.47, a mol ratio of silica to alumina of about 7:1, up to about 2% by weight of moisture and up to about 10% by weight of sodium oxide. Typically, this material has a particle size of up to about 35 microns, preferably about 1–20 microns. The preferred moisture content is about 10–20% by weight, measured by loss at 105°C. and the typical content of sodium oxide is about 5–10% by weight. Generally, the agent has a loose bulk density of up to about 0.2 g/cc, preferably about 0.07–0.12 g/cc.

The transparent toothpaste may also contain surface active agent, e.g. to achieve increased prophylactic action, assist in achieving thorough and complete dispersion of the instant compositions throughout the oral cavity, and render the instant compositions more cosmetically acceptable. The organic surface active material may be anionic, nonionic, ampholytic, or cationic in nature, and it is preferred to employ as the surface active agent a detersive material which imparts to the composition detersive and foaming properties. Suitable types of such detergents are water soluble salts of higher fatty acid monoglyceride monosulfates, such as sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1,2 hydroxy propane sulfonates, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl or N-palmitoyl sarcosine, which should be substantially free from soap or similar higher fatty acid material which tends to substantially reduce the effect of these compounds. The use of these sarcosine compounds in dentifrice compositions of the present invention is particularly advantageous since these materials exhibit a prolonged and marked effect in the inhibition of acid formation in the oral cavity due to carbohydrates breakdown in addition to exerting some reduction in the solubility of tooth enamel in acid solutions. Desirable surface-active effect is obtained with a long chain fatty acid monoglyceride sulfonate such as the sodium salt of hydrogenated coconut oil fatty acid monoglyceride sulfonate used alone or in combination with sodium lauryl sulfate.

Other particularly suitable surface active materials include nonionic agents such as condensates of sorbitan monstearate with approximately 60 moles of ethylene oxide, condensates of ethylene oxide with propylene oxide condensates of propylene glycol ("Pluronics") and amphoteric agents such as quaternized imidazole derivatives, which are available under the trademark "Miranol" such as Miranol $C_2M$. Cationic surface active germicides and antibacterial compounds such as di-isobutylphenoxyethoxyethyl dimethyl benzyl ammonium chloride, benzyl dimethyl stearyl ammonium chloride, tertiary amines, having one fatty alkyl group (of from 12 to 18 carbon atoms) and two (poly) oxyethylene groups attached to the nitrogen (typically containing a total of from about 2 to 50 ethanoxy groups per molecule) and salts thereof with acids, and compounds of the structure

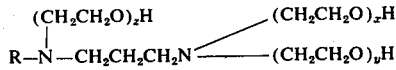

where R is a fatty alkyl group containing from about 12 to 18 carbon atoms, and $x$, $y$ and $z$ total 3 or higher, as well as salts thereof with mineral organic acids, may also be used. It is preferred that the total amount of surface-active agent be about 0.05–5% by weight, preferably about 1–3%, of the dentifrice.

Various other materials may be incorporated in the oral preparation of this invention. Examples thereof are coloring or whitening agents, preservatives, silicones, chlorophyll compounds, ammoniated materials, such as urea, diammoniumphosphate and mixtures thereof, and other constituents. Each of these adjuvants may be typically incorporated in the instant toothpastes in amounts up to about 5%.

The toothpaste may also contain antibacterial agents in amounts of about 0.01–5%. Typical examples of such agents are guanidines, biguanides and amines such as:

$N^1$-(4-chlorobenzyl)-$N^5$-2,4-(dichlorobenzyl) biguanide;
  p-chlorophenyl biguanide;
  4-chlorobenzhydryl biguanide;
  4-chlorobenzhydrylguanylurea;
  N-3-lauroxypropyl-$N^5$-p-chlorobenzylbiguanide;
  1,6-di-p-chlorophenylbiguanidohexane;
  1-(lauryldimethylammonium)-8-(p-chlorobenzyldimethylammonium) octane dichloride;
  5,6-dichloro-2-guanidinobenzimidazole;
  $N^1$-p-chlorophenyl-$N^5$-laurylbiguanide;
  5-amino-1,3-bis(2-ethylhexyl)-5-methylhexahydropyrimidine; and their non-toxic acid addition salts.

Suitable flavoring or sweetening sialagogues may be employed in formulating a flavor for the compositions of the present invention. Examples of suitable flavoring constituents include the flavoring oils, e.g., oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate and saccharine. Suitably, flavor and sweetening agent may together comprise from about 0.01 to 5% or more of the compositions of the instant invention. Chloroform may be employed to modify the flavor.

The compositions of the present invention suitably may also contain a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride ($SnF_2 \cdot KF$), sodium hexafluorostannate, stannous chlorofluoride, sodium fluorozirconate and sodium monofluorophosphate. These materials, which dissociate or release fluorine-containing ions in water, suitably may be present in an effective but non-toxic amount, usually within the range of about 0.01 to 1% by weight of the water soluble fluorine content thereof.

The iridescent flakes used in the practice of this invention are generally present in amount of up to about 5%, preferably less than 3%, of the weight of the transparent toothpaste in which they are dispersed. A particularly suitable product is obtained when the iridescent flakes are mother of pearl flakes (a true nacreous secretion found on the inner surfaces of oyster shells and made up of non-toxic $CaCO_3$). These mother of pearl flakes refract light in various wave lengths across the color spectrum and their incorporation in the transparent toothpaste (e.g. in proportions in the range of about 1½ to 3%, preferably about 2%, for example about 1¾ to 2¼%) results in a multicolored speckled effect with the clarity of the transparent gel intact, giving a beautiful sparkle. In use, when one extrudes the product from a conventional toothpaste tube onto the toothpaste, the resulting extrudate (which usually has a thickness in the range of about 4 to 8 mm) is typically clear with visible spaced light refracting sparkling dots; as the extrudate is moved, relative to the eye of the observer, different dots become visible and the apparent colors of individual dots changes. Especially good results have been obtained with mother of pearl flakes screened so that they are retained on a 100 mesh (U.S. Standard) sieve (corresponding to a particle size of about 149 microns) and pass through a 30 mesh sieve (corresponding to a particle size of about 590 microns) with the predominant portion being larger than 200 microns.

The mother of pearl flakes can be produced by grinding oyster shells and mechanically separating the mother of pearl flakes from the balance of the ground material, as by flotation. Typically, the mother of pearl flakes are flat, smooth-surfaced, less than 50 microns thick (e.g. 10–40 microns), oval-shaped in plane view, and made up of numerous thin parallel layers (e.g. of thickness well below a micron to say 2–3 microns).

Another type of iridescent flake comprises thin transparent mica flakes coated with a thin layer of titanium dioxide. One type of such flakes or platelets has a $TiO_2$ content of about 17%, an average thickness of less than 1 micron (e.g. 0.7 micron), with the longest dimension of most of the platelets being less than about 100 microns, e.g., about 15 to 40 microns, the refractive index of the mica layer being about 1.58 and the refractive index of the TiO₂ layer being about 2.3. When these are incorporated into the transparent toothpaste in proportion in the range of about 0.1 to 0.3%, preferably about ¼%, the extrudate from the toothpaste tube is also sparkling, with the individual reflecting and iridescent dots being very small and close together, giving an overall opaque pearlescent effect. Still another but less desirable type of iridescent flakes comprises mica flakes carrying the coating of another material (namely BiOCl) whose refractive index is different from that of the mica.

By variation in particle concentration one can produce different effects. One may also use mixtures of various types of the flakes.

It is found, surprisingly, that the presence of the iridescent flakes not only imparts a unique esthetic appearance but also gives a substantial improvement in the properties of the dentifrice such as its ability to remove stains from the teeth. Certain iridescent flakes also substantially improve the polishing capability of the dentifrice in which they are present.

The transparent toothpaste may be prepared in well known manner. Thus, a gelling agent such as sodium carboxymethyl cellulose or Carbopol 934 and a preservative such as sodium benzoate, if employed, is dispersed with a humectant such as glycerine. Water may also be present. Additional humectant and water, as an aqueous 70% sorbitol solution, may then be mixed with the dispersion and heat applied at about 40°–65°C., say 50°C., to form a paste, gel or cream. Polishing agent is then added. Surface-active agent, such as sodium lauryl sulfate, if employed, is then dispersed in the mixture. The preparation is then cooled and desired flavor may be added.

The iridescent flakes are then dispersed in the toothpaste with minimal mechanical agitation, insufficient to substantially break them down. The toothpaste is then thoroughly deaerated (e.g. in vacuo) and tubed.

In the manufacture of dentifrices, it is conventional to remove entrained air from the product by de-aeration under vacuum typically at a late stage in the manufacture. In an aspect of the instant invention, it has been observed that in clear dentifrice gels of suitable viscosity, the dispersed, immobile air bubbles desirably enhance the appearance of the dentifrice, and can, therefore, be permitted to remain. Alternatively, the air can be replaced with another gas in nontoxic quantity, such as nitrogen or carbon dioxide. In particular, carbon dioxide can provide an effervescent character to the dentifrice.

In the event it is desired to have a minimum amount of air in the dentifrice, or only to have to remove a minimum amount of air from the dentifrice of the instant invention, the "Unimix" apparatus described in "Process Engineering" Sept. 11, 1970, pages 81–85, is particularly efficacious for this purpose. In this apparatus a mixing tool can be rotated in clockwise or counterclockwise mannter, and the action of the mixing tool is followed by the action of a scraper blade to ensure that the working surface of the apparatus is scraped clean. Preferably, a plastic such as polytetrafluorethane is used as the scraper since it is compatible with the various ingredients of the dentifrice. The positioning of the mixing tool and the scraper from a raised central column in the apparatus and the further presence of a hydraulically operated vacuum tight lid permits but little air to enter the formulation during processing. Thus, gelling agent and a portion of liquid including water and/or humectant can be efficiently blended in the Unimix apparatus. Then the remaining liquid can be separately blended with the polishing agent and additional components (except for post-added components, such as flavouring oil) in the Unimix, and then the two dispersions blended together in the Unimix apparatus. If desired, the small amount of air can be largely removed under the depressurised conditions in the apparatus. The apparatus can be used to blend ingredients at room temperature as well as at higher temperatures.

The following Examples are given to illustrate this invention further. In this application all proportions are by weight unless otherwise indicated and all sieve sizes are U.S. Standard.

EXAMPLE 1

A transparent toothpaste having the following formulation is prepared:

glycerine 25%; aqueous 70% solution of sorbitol 40%; cellulose gum (sodium carboxymethyl cellulose) 0.35%; colloidal silica (thickener, e.g. Cab-o-sil M5 manufactured by Cabot Corporation or Syloid 244, manufactured by Grace, Davison Chemical Co., having a bulk density of 0.11 g/cm³) 3½%; Syloid 74, 18%, detergent (sodium lauryl sulfate) 2%; added water about 6%; the balance being a trace of blue dye (e.g. 0.1% of F. D. and C, blue 1, added as a 1% aqueous solution), preservatives and flavors. This transparent toothpaste is mechanically blended with 2% of mother of pearl flakes (of a size, previously described, retained on a 100 mesh sieve and passing through a 40 mesh sieve) When the resulting transparent sparkling toothpaste is tested for its ability to remove stains from human dental enamel it is found to be about 34% more effective than a similar toothpaste free of the mother of pearl flakes.

In the stain removal test, sections of human dental enamel are etched with 0.1N HCl for 2 minutes, rinsed with water, then wet with a dilute solution of stannous fluoride, wiped dry, and finally exposed to a stream of hydrogen sulfide gas which results in the deposition of a brown deposit of stannous sulfide. The amount of stain on the surface is measured with a Gardner Automatic Color Difference meter. The surface is then brushed with a mechanical brushing machine for 3000 reciprocal strokes with a slurry of a dentifrice and the residual stain measured with the meter. Finally, the stain which remains is completely removed with dental pumice and the reflectance of this surface is read. The ability of a dentifrice to remove the stain is expressed by Equation 1.

$$\text{Equation 1) Percent Stain Removed} = \frac{(R_d \text{ 3000 strokes} - R_1 \text{ initial}) \, 100}{R_d \text{ pumiced} - R_d \text{ initial}}$$

Where $R_d$ initial, $R_d$ 3000 strokes, and $R_d$ pumiced are respectively the reflectance values measured on the initially stained surface, after brushing for 3000 reciprocal strokes and after removing the residual stain by pumicing.

EXAMPLE 2

Example 1 is repeated using 0.25% of the $TiO_2$ coated mica flakes previously described in place of the mother of pearl flakes. An opaque cream having a pearlescent character is obtained, which has stain removal properties similar to those of Example 1.

EXAMPLE 3

Example 1 is repeated, using 0.25% of Rona MP10 flakes ($TiO_2$-coated mica flakes, the longest dimensions of most platelets being about 50–80 microns).

In the preferred embodiments of the invention a clear transparent toothpaste is used as the matrix in which the flakes are dispersed. Typically the transparency of the matrix is such that one can easily read ordinary print (e.g. newspaper print) through an 8mm thick extrudate of the transparent toothpaste. It is within the broader scope of the invention, however, to add the flakes to a matrix which is somewhat hazy, or less desirably, merely translucent or even opaque, and to use larger proportions of the flakes (e.g. 10% or 15% or more) to give an iridescent or sparkling effect. Opaque matrices may contain polishing agents well known in the art, whose index of refraction is considerably different from that of the vehicle, e.g. $Al_2O_3·3H_2O$, $Ca_2H-PO_4·2H_2O$, chalk, etc. It is also within the broader scope of the invention to incorporate the pearlescent flakes into dentifrices other than toothpastes, e.g. toothpowders and crushable tooth tablets.

As is well known mother of pearl (nacro) consists of prismatic psuedo hexagonal aragonite ($CaCO_3$ of refractive index 1,6809) crystals oriented so that the long crystallographic axis is at right angles to plane of the platelets which are held together by conchiolin, a hornlike organic secretion.

It will be noted that the preferred pearlescent materials have parallel layers which are less than 1 micron in thickness and which produce interference colors by refraction of light. The indices of refraction of these materials are generally different from the index of refraction of the transparent toothpaste; for instance in one preferred embodiment the latter is about 1.4–1.5.

EXAMPLE 4

The following transparent toothpaste is blended with 2% of mother of pearl flakes of a size such that 100% are retained in a low mesh sieve while passing trough a 40 mesh sieve:

Toothpaste

| Component | Parts |
|---|---|
| Glycerine | 15 |
| Sorbitol (70%) | 45 |
| Sodium carboxymethyl cellulose | 0.7 |
| Syloid 244 | 5 |
| Sodium aluminosilicate | 16 |
| Sodium lauryl sulfate | 2 |
| Sodium benzoate | 0.5 |
| Sodium saccharine | 0.2 |
| Color | 0.2 |
| Flavor | 1 |
| Chloroform | 2.5 |
| Water | 3 |

EXAMPLE 5

Example 2 is repeated using 0.3% of $TiO_2$ coated mica flakes of 15 to 40 micron particle size having a platelet thickness of 0.7 micron and an anatase coating on both sides of each mica flake, and containing about 20% $TiO_2$ and about 80% mica. The composition also contains 2% chloroform, 0.17% sodium saccharin, 0.5% sodium benzoate, 1% of flavor (essential oil), 0.09% of a 1% aqueous solution of F D and C Blue 1, 0.09% of a 1% aqueous solution of F D and C Yellow 5, and 7.6% of added water. The resulting sparkling transparent green toothpaste has excellent enamel polishing characteristics.

Further embodiments of the invention will be apparent to one skilled in the art from the above description.

What is claimed is:

1. A toothpaste containing about 0.1 to 5% of non-toxic iridescent mother of pearl flakes, which flakes are about 10–50 microns thick and about 149 to 590 microns in particle size and are dispersed in a transparent toothpaste matrix.

2. The toothpaste claimed in claim 1 wherein said toothpaste contains a dental polishing agent.

3. The toothpaste claimed in claim 1 wherein said mother of pearl flakes are present in amount of about 1½ to 3% by weight and said toothpaste when extruded as a ribbon 4 to 8mm thick is clear with visible spaced light refracting sparkling dots.

4. The toothpaste claimed in claim 2 wherein said polishing agent is selected from the group consisting of porous amorphous silicic anhydride and complex sodium aluminosilicate.

5. A method for treating dental enamel to reduce stain which forms thereon comprising brushing the surface of said human dental enamel bearing stain which forms thereon with a dentifrice containing a stain reducing amount of non-toxic iridescent flakes of mother of pearl, which flakes are 10–50 microns thick and have a particle size distribution between 149–590 microns for a time sufficient to reduce said stain.

6. The method for treating dental enamel as in claim 5 in which said flakes are dispersed in a toothpaste which when extruded as a ribbon about 4 to 8 mm thick is clear with visible spaced light refractive sparkling dots.

* * * * *